(12) United States Patent
Nobutani et al.

(10) Patent No.: US 7,856,975 B2
(45) Date of Patent: Dec. 28, 2010

(54) LIQUID MEDICINE EJECTION DEVICE

(75) Inventors: Toshiyuki Nobutani, Yokohma (JP); Mitsuru Imai, Chichibu (JP)

(73) Assignee: Canon Kabushiki Kaisha, Tokyo (JP)

( * ) Notice: Subject to any disclaimer, the term of this patent is extended or adjusted under 35 U.S.C. 154(b) by 832 days.

(21) Appl. No.: 11/469,142

(22) Filed: Aug. 31, 2006

(65) Prior Publication Data

US 2007/0062520 A1    Mar. 22, 2007

(30) Foreign Application Priority Data

Sep. 13, 2005    (JP) .............................. 2005-265129

(51) Int. Cl.
*A61M 11/00* (2006.01)
(52) U.S. Cl. .......................... 128/200.14; 128/200.22; 128/204.18
(58) Field of Classification Search ................. 128/200.14–200.23, 204.18; 604/212
See application file for complete search history.

(56) References Cited

U.S. PATENT DOCUMENTS

| | | | | |
|---|---|---|---|---|
| 5,404,871 A | * | 4/1995 | Goodman et al. | ...... 128/200.14 |
| 6,196,219 B1 | * | 3/2001 | Hess et al. | ............. 128/200.21 |
| 2001/0042927 A1 | * | 11/2001 | Rock | .......................... 261/79.1 |
| 2002/0046750 A1 | * | 4/2002 | Gonda et al. | ........... 128/200.14 |
| 2002/0065685 A1 | * | 5/2002 | Sasaki et al. | ................... 705/3 |
| 2004/0050383 A1 | * | 3/2004 | Cox et al. | .............. 128/200.14 |

FOREIGN PATENT DOCUMENTS

| | | |
|---|---|---|
| WO | WO 95/01137 | 1/1995 |
| WO | WO 02/04043 A2 | 1/2002 |

\* cited by examiner

*Primary Examiner*—Steven O Douglas
*Assistant Examiner*—Valerie Skorupa
(74) *Attorney, Agent, or Firm*—Fitzpatrick, Cella, Harper & Scinto (57) ABSTRACT

There is provided a liquid medicine ejection device to eject liquid medicine into an inhalation flow path in the form of liquid droplets, thereby to allow a user to inhale the liquid medicine through a suction portion. In the liquid medicine ejection device is an ejection means, which communicates with a liquid medicine storage section, for ejecting the liquid medicine in the form of liquid droplets from an ejection opening. A pressure variable means changes a pressure in the liquid medicine storage section in accordance with a change of pressure in the inhalation flow path connected to the ejection opening of the ejection means and the suction portion. According to the liquid medicine ejection device of the present invention, it is possible to prevent ejection failure caused by a negative pressure applied to the ejection means, thereby enabling reliable inhalation.

12 Claims, 5 Drawing Sheets

LIQUID MEDICINE EJECTION DEVICE

BACKGROUND OF THE INVENTION

1. Field of the Invention

The present invention relates to a liquid medicine ejection device, and more particularly, to an ejection device or an inhaler for ejecting liquid medicine such as medical agent in the form of liquid droplets and allowing a user to inhale the liquid medicine.

2. Description of the Related Art

The recent advancements of medicine and science have increased average life expectancy, leading to aging of society. On the contrary, along with changes of eating habits and living environment and progress in environmental pollution, new diseases and infectious diseases due to viruses and fungi have been found, which contributes to people's growing concern for their health. In particular, in the so-called developed countries, an increase in the number of patients suffering from adult diseases such as diabetes and high blood pressure has been a problem.

On the other hand, the number of medical institutions has not increased to an extent capable of dealing with this increase in the number of patients. There are some areas where people have no access to medical institutions. Therefore, there have been concerns about providing remedies in the future including taking political measures.

For example, considering diabetics, the number of whom is currently increasing, a patient suffering insulin-dependant diabetes mellitus, called "type I", has a pancreas that does not secrete insulin, and therefore it is required to have insulin administered to that patient at regular intervals. The administration of insulin is performed through hypodermic injection at present, which imposes substantial physical and mental strain on the user.

In order to reduce this strain on the user, a pen-shaped injector has been developed, which employs a fine needle so as to give little pain to the user. However, in many cases, patients suffering type I diabetes live a life which is the same as that of able-bodied people, except for the need to have insulin administered at regular intervals. Thus, even if the injector has a pen shape, the patients may feel mentally uncomfortable performing the injection in front of other people, which makes it difficult for them to carry out the administration at appropriate timings. As a result, according to the method described above, there is a risk of the appropriate treatment not actually being delivered to the user.

On the other hand, a treatment for the user in which a medicine ejection device that allows the user to intake medicine through inhalation is utilized in combination with an information database such as electronic clinical recording is being embodied. Such a medicine ejection device also serves as a mobile terminal that is combined with a storage means for storing individual information including clinical recording and a prescription for the user which relates to the user, and with the ejection device for ejecting medicine in the form of fine liquid droplets to allow the user to inhale the medicine. Further, the medicine ejection device includes, so as to allow the user to inhale medicine according to the information in the prescription, an ejection control means for controlling the ejection device to eject the medicine based on an inhalation profile of the user (refer to International Publications Nos. WO 95/01137 and WO 02/04043).

Such a medicine ejection device is required to be capable of accurately managing a dosage and administration intervals of the medicine according to the prescription, performing appropriate ejection control in accordance with the inhalation profile of each user, and effectively administering the medicine.

As regards such an ejection device, there is devised a method of ejecting a predetermined number of appropriate small droplets from a discharge orifice (ejection opening) into an air flow to be inhaled from the mouthpiece or the like, by using a force generated by a bubble generating heater or a piezoelectric element provided to the ejection head, thereby making it possible to eject grains (droplets or particles) that are uniform in diameter. However, the ejection head tends to be directly applied with the negative pressure generated at the time of inhalation, and when the negative pressure value becomes too large (that is, the pressure becomes too low), there is a fear that liquid leakage from the orifice may occur at the time of inhalation. In a case where such liquid leakage occurs, it is difficult to eject droplets appropriately small enough. Further, it is feared that the orifice may be closed, so that the ejection from the orifice is difficult to perform, which leads to a fear that the predetermined amount of medicine may not be ejected.

As a countermeasure to solve the above-mentioned problem, it is conceivable to employ an approach involving constantly applying a negative pressure in a medicine storage section. However, if the negative pressure is too much larger than the negative pressure generated through the inhalation in the inhalation flow path, there is a fear that ejection may become impossible. Further, the inhalation rate of a user is not constant, so the negative pressure applied to the ejection head is not constant either, which leads to a fear that this variation in negative pressure may significantly affect ejection properties (such as granule diameter and ejection quantity).

SUMMARY OF THE INVENTION

The present invention is directed to an ejection device having a structure in which an ejection failure that may be caused due to a negative pressure applied to an ejection means is prevented, thereby to enable a reliable inhalation. The ejection device of the present invention is a liquid medicine ejection device for ejecting liquid medicine into an inhalation flow path in the form of liquid droplets to allow a user to inhale the liquid medicine. The liquid medicine ejection device includes a liquid medicine storage section, and an ejection head communicating with the liquid storage section, for ejecting the liquid medicine from an ejection opening in the form of liquid droplets and a pressure changer for changing a pressure in the liquid medicine storage section in accordance with a change in pressure in the inhalation flow path.

According to the liquid medicine ejection device of an embodiment of the present invention, it is possible to adjust the pressure in the liquid medicine storage section connected to the ejection means depending on each user's inhalation, thereby making it possible to realize the ejection device having a structure that prevents ejection failure due to the negative pressure applied to the ejection means, thereby enabling a reliable inhalation.

Other features and advantages of the present invention will be apparent from the following description taken in conjunction with the accompanying drawings, in which like reference characters designate the same or similar parts throughout the figures thereof.

DETAILED DESCRIPTION OF THE INVENTION

Figure 1:
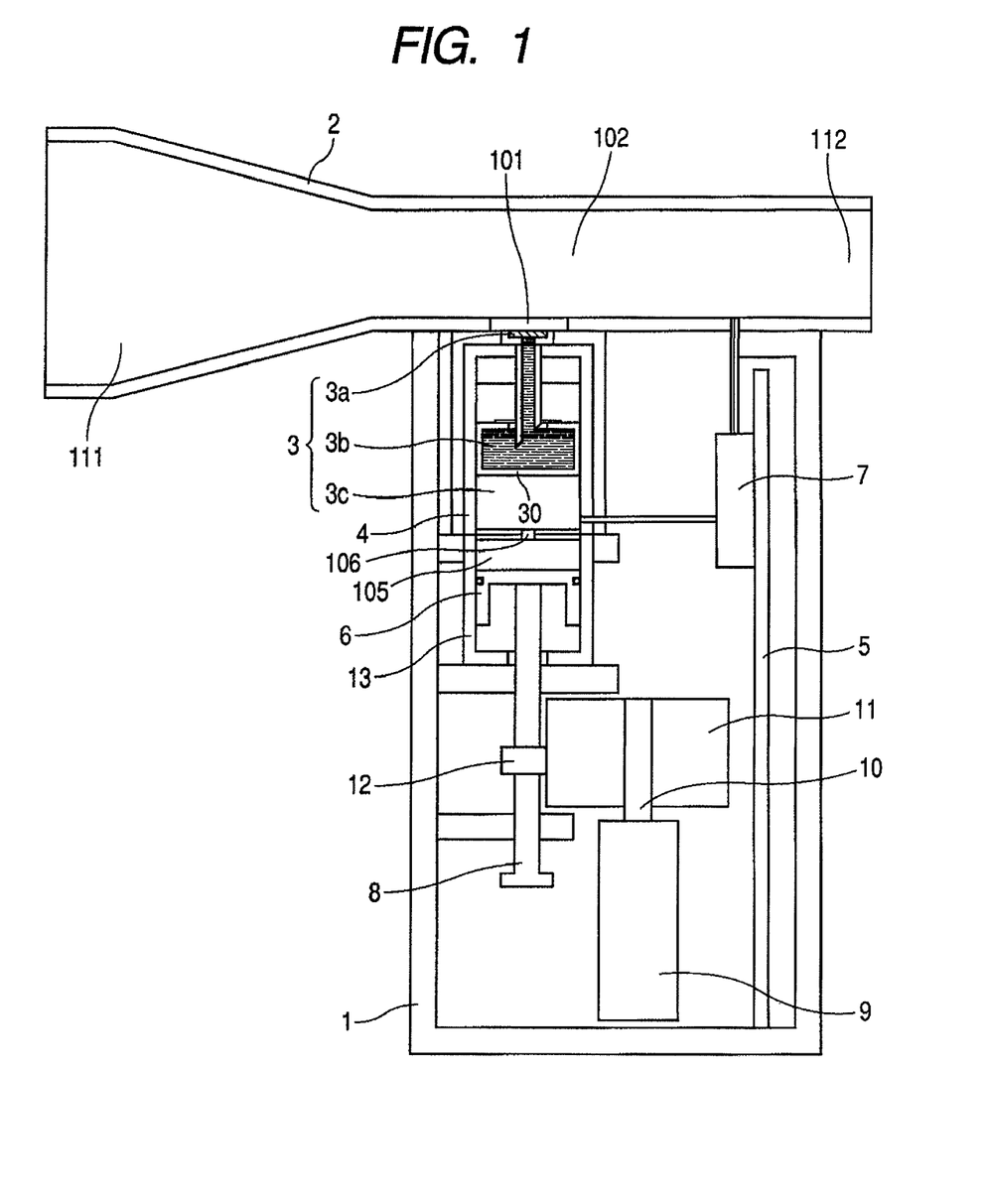
FIG. 1 is a sectional view showing an ejection device according to a first embodiment of the present invention.

Hereinafter, an embodiment of the present invention will be described. The description is made with reference to FIG. 1 as appropriate. FIG. 1 illustrates a first embodiment of the present invention, which will be described later. An ejection device or an inhaler according to the present invention is structured so as to be portably held by a user, and includes a storage means for storing individual information including clinical recording and a prescription of the user which relates to the user. The ejection device or inhaler is an ejection device which includes an ejection means 3a for enabling ejection of medicine in a fixed quantity in the form of fine liquid droplets having high uniformity in particle size, which allows the user to inhale the medicine. The ejection means 3a is a thermal ink jet head or a piezoelectric ink jet head. While the inhaler is in use, it is possible to attach a mouthpiece 2, a tank 3b, and the ejection head (i.e., ejection means) 3a to an ejection device main body so as to be detachable from the ejection device main body. The mouthpiece 2 has a suction portion through which inhalation is performed. The tank 3b contains the liquid medicine. The ejection head 3a ejects the medicine in the form of fine liquid droplets, the medicine being supplied from the tank. With this construction, in accordance with information on the prescription, the user can effectively and sanitarily inhale the medicine. An inhalation flow path 102 formed by the mouthpiece 2 is the only flow path in the entire ejection device.

On the other side of the liquid medicine tank 3b with respect to the ejection head 3a, there is provided an air pocket (i.e., fluid chamber or air chamber 3c). In a border portion between the air chamber 3c and the liquid medicine tank 3b, a part of the liquid medicine tank 3b is formed of a flexible film 30 which easily deforms due to a pressure in the air chamber 3c to thereby change a pressure in the liquid medicine tank 3b. Such the structure relates to a pressure variable means (pressure changer).

When a detection means detects a negative pressure generated by an inhalation flow in the inhalation flow path of the mouthpiece and the liquid medicine is ejected from the ejection head after the user starts inhalation, in accordance with a change in pressure inside the inhalation flow path 102, the pressure in the air chamber 3c is changed by the pressure variable means. As a result, the pressure in the liquid medicine tank is changed.

When the user starts inhalation, the pressure in the inhalation flow path 102 decreases, thereby causing the negative pressure. Here, when a difference between the pressure in the inhalation flow path 102 and the pressure in the liquid medicine tank 3b deviates from a predetermined pressure difference by about 0.02 kPa or more, the pressure in the air chamber 3c is decreased in order to also decrease the pressure in the liquid medicine tank. As the pressure in the air chamber 3c is decreased as described above continuously, the pressure in the liquid medicine tank becomes too low to achieve the predetermined pressure difference. Accordingly, the pressure variable means capable of adjusting the pressure in the liquid medicine tank performs a pressure adjustment such that the pressure difference between the pressure in the inhalation flow path 102 and the pressure in the liquid medicine tank 3b is about ±0.03 kPa (i.e., the predetermined pressure difference). The above numerical value, 0.03 kPa, is decided in advance according to the accuracy of a sensor 7. Therefore, the numerical value may vary according to performance of the sensor 7. Thus, even if the negative pressure in the inhalation flow path 102 varies according to a change in inhalation quantity, the liquid medicine does not leak out from the ejection opening of the ejection head.

Further, it is preferable to perform the pressure adjustment such that the pressure in the liquid medicine tank 3b is larger to a positive pressure side than the pressure in the inhalation flow path 102 by 0.1 kPa. As a result, a refilling property of the liquid medicine from the liquid medicine tank to a head nozzle portion can be improved, thereby also making it possible to increase an ejection frequency. At this time, it is possible to provide a small ejection head capable of ejecting a large quantity of medicine within a relatively short time, thereby making it possible to complete the inhalation in a short time. The ejection head ejects the medicine, so in order to use the ejection head sanitarily, the user throws the ejection head away after one to several uses, in the same manner as with an injection needle. Accordingly, an ejection head preferable for the user is the one which is small, capable of ejecting a large quantity of medicine, and cheap. With regard to the pressure adjustment, although depending upon the structure of the device, the pressure in the liquid medicine tank 3b is preferably made larger on the positive pressure side than that in the inhalation flow path 102 by about 0 to 0.5 kPa. If the pressure in the liquid medicine tank 3b is made larger than that on the positive side by more than 0.5 kPa, there is a risk of the liquid medicine leaking out from the head nozzle portion.

According to the above-mentioned embodiment, the user's mental/physical strain is reduced, and the user can appropriately inhale the medicine with a simple operation. Further, it is possible to provide an ejection device in which ejection of the medicine is managed accurately according to the prescription and the user can accurately and efficiently inhale the medicine with a simple operation according to the prescription of the medicine.

EMBODIMENTS

Hereinafter, embodiments of the present invention will be described in detail with reference to the drawings.

FIG. 1 is a sectional view for explaining the first embodiment of an ejection device. In this embodiment, the mouthpiece 2 can be fixed to a main body case 1 so as to be detachable therefrom. The mouthpiece 2 has a hole 101 connected thereto in order for the ejection liquid droplets to be ejected from a medicine ejection unit 3 into the inhalation flow path 102 inside the mouthpiece. Further, the mouthpiece 2 is provided with a suction portion 111 and an air intake opening 112 formed therein. Facing the hole 101 provided to the mouthpiece 2, the ejection head 3a of the medicine ejection unit 3 is arranged. The medicine ejection unit 3 includes the ejection head 3a, the liquid medicine tank 3b partially formed of the flexible film 30 and containing a liquid medicine therein, and the air chamber 3c, which are integrated with each other. The medicine ejection unit 3 is attached to a medicine ejection unit attachment portion 4 of the main body case 1 so as to be detachable. On a lower side of the attachment portion 4, there is provided a cylinder-shaped piston guide 13 for holding a piston 6 for varying a volume of the air chamber 3c of the ejection unit 3.

The air chamber 3c is connected to one of two pressure measuring holes of a differential-pressure sensor 7 arranged on a control board 5. The other of the pressure measuring holes of the differential-pressure sensor 7 is connected to the inside of the inhalation flow path 102 of the mouthpiece 2. It is preferable that the latter pressure measuring hole measure a pressure at a portion inside the inhalation flow path 102 indicating substantially the same pressure as that in the inhalation flow path at a position of the ejection opening of the ejection head 3a. In this case, it is preferable that the pressure measuring hole be provided near the ejection opening. In a structure of FIG. 1, while the ejection opening of the ejection head 3a and the portion connected to the pressure measuring hole are spaced apart from each other to some extent, an inner wall of the inhalation flow path 102 therebetween is flat, so pressures at the ejection opening and the above-mentioned portion are substantially the same, causing no problem. The air chamber 3c is also connected to a space 105 in an upper portion of the piston guide 13 through a hole 106 formed in a partition wall.

Further, as long as it is possible to estimate the pressure in the flow path at a position of the ejection opening, arrangement of pressure measuring means such as the pressure measuring hole is not limited to the portion near the ejection opening. For example, even if the inhalation flow path 102 is not flat and has a shape such as a tie between the pressure measuring hole and the position of the ejection opening, the pressures at the pressure measuring hole and the above-mentioned position at a time of inhalation have a relative relationship. Accordingly, if the relative relationship is obtained empirically or is calculated in advance, on the basis of this, the pressure at the position of the ejection opening can be calculated from the pressure at the pressure measuring hole.

The piston 6 is fixed to a piston shaft 8. An outer peripheral surface of the piston shaft 8 is threaded to be engaged with a thread cut in an inner peripheral surface of a pinion 12. When the pinion 12 rotates at a fixed position, the piston shaft 8 moves vertically. Accordingly, a rotary motion of a gear 11 fixed to a motor shaft 10 for a pressure adjusting motor 9 is transmitted to the piston shaft 8 as the vertical movement of the piston shaft 8 through rotations of the pinion 12 engaged with the piston shaft 8. In this way, the piston shaft 8 and the piston 6 reciprocate owing to positive/counter rotations of the pressure adjusting motor 9.

The ejection head 3a is electrically connected to the control board 5 and the liquid droplet ejection thereof is controlled. The ejection head 3a, the control board 5, the pressure adjusting motor 9, and other electrically driven portions are driven through electrification from a battery (not shown) built in the main body case 1.

Operations and actions of this embodiment having the above-mentioned construction will be described.

First, the user attaches the medicine ejection unit 3 and the mouthpiece 2 to the main body as shown in FIG. 1. At this time, owing to an attachment detection function of the main body (for example, in a case where the medicine ejection unit 3 performs ejection through a thermal ink jet method, the function can be achieved by measuring a resistance value of a heater serving as an ejection energy generating means), a power of the main body is turned on. As a matter of course, the medicine ejection unit 3 may be of a type employing a piezoelectric element.

Next, when the user starts inhalation, the pressure in the inhalation flow path 102 of the mouthpiece 2 changes to the negative pressure side. In this embodiment, when a negative pressure exceeds a certain threshold value, it is judged that the inhalation is started (here, the detection of the negative pressure may be performed by the differential-pressure sensor 7 or by another negative pressure sensor), and the ejection from the ejection unit 3 is started. At this time, as a matter of course, an orifice surface on a surface of the ejection head 3a is also subjected to the negative pressure, thereby generating a force in a direction in which a liquid leaks out. In order to cancel the force, based on the detected value of the differential-pressure sensor 7, the pressure in the air chamber 3c is changed so as to be reduced to the negative pressure side. That is, the pressure adjusting motor 9 is rotated in such a direction that increases the volume of the air chamber 3c, and the rotation of the gear 11 is transmitted through the pinion 12 to move the piston shaft 8 and the piston 6 downwards. The pressure balance is set such that the pressure in the air chamber 3c is higher than the pressure in the inhalation flow path 102 by about 0.1 kPa.

In contrast, when a flow rate in the inhalation flow path 102 decreases and the pressure therein approaches atmospheric pressure, the pressure adjusting motor 9 is rotated backward to perform control so as to increase the pressure in the air chamber 3c. That is, the pressure adjusting motor 9 is rotated in such a direction as to reduce the volume of the air chamber 3c to move the piston shaft 8 and the piston 6 upwards. Again, the pressure in the air chamber 3c is adjusted to be higher than the pressure in the inhalation flow path 102 by about 0.1 kPa. During the inhalation by the user, the above-mentioned actions are repeated.

Based on the data in the prescription, the ejection device main body judges that the predetermined amount has been ejected and notifies the user of the completion of the inhalation by emitting a completion signal such as light, sound, or vibration.

The pressure in the air chamber 3c is set to be higher than the pressure in the inhalation flow path 102 by about 0.1 kPa, thereby making it possible to repeat ejection and refilling to eject a desired ejection amount of the medicine. Therefore, it is also possible to increase the ejection frequency. As a result, it is also possible to complete the ejection in a short time using a small ejection head having a small number of nozzles. As described above, it is effective for enhancing the refilling property to adjust the pressure in the air chamber to be higher than the pressure in the inhalation flow path by about 0.1 kPa, in order to solve the problem in that refilling could otherwise lag behind the ejection frequency, thereby causing misfiring. The above-mentioned action can be performed by controlling the pressure variable means (composed of the air chamber 3c, the differential-pressure sensor 7, the piston 6, the pressure adjusting motor 9, and the like), etc., based on a program for performing the procedure described above.

Figure 2:
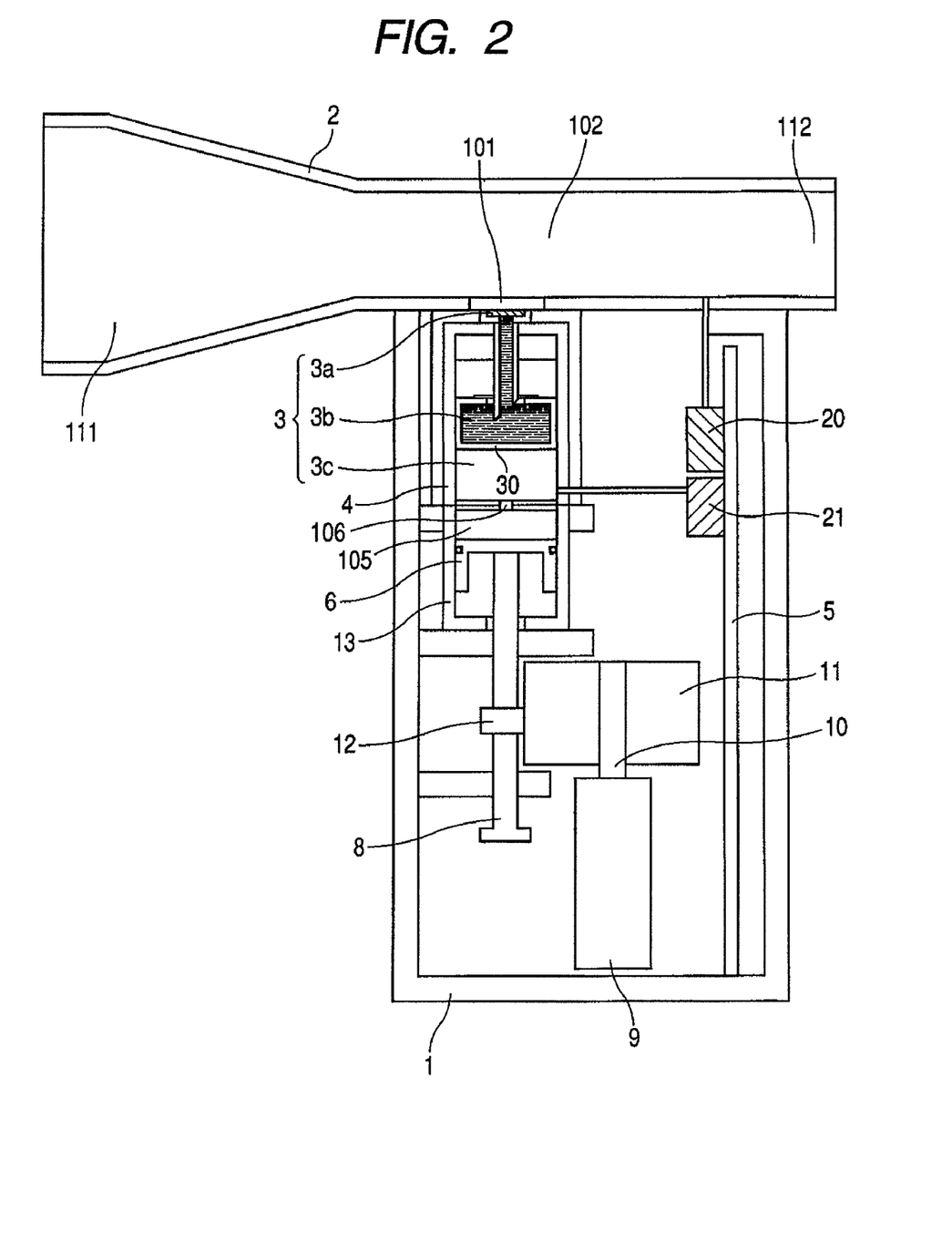
FIG. 2 is a sectional view showing an ejection device according to a second embodiment of the present invention.
Figure 3:
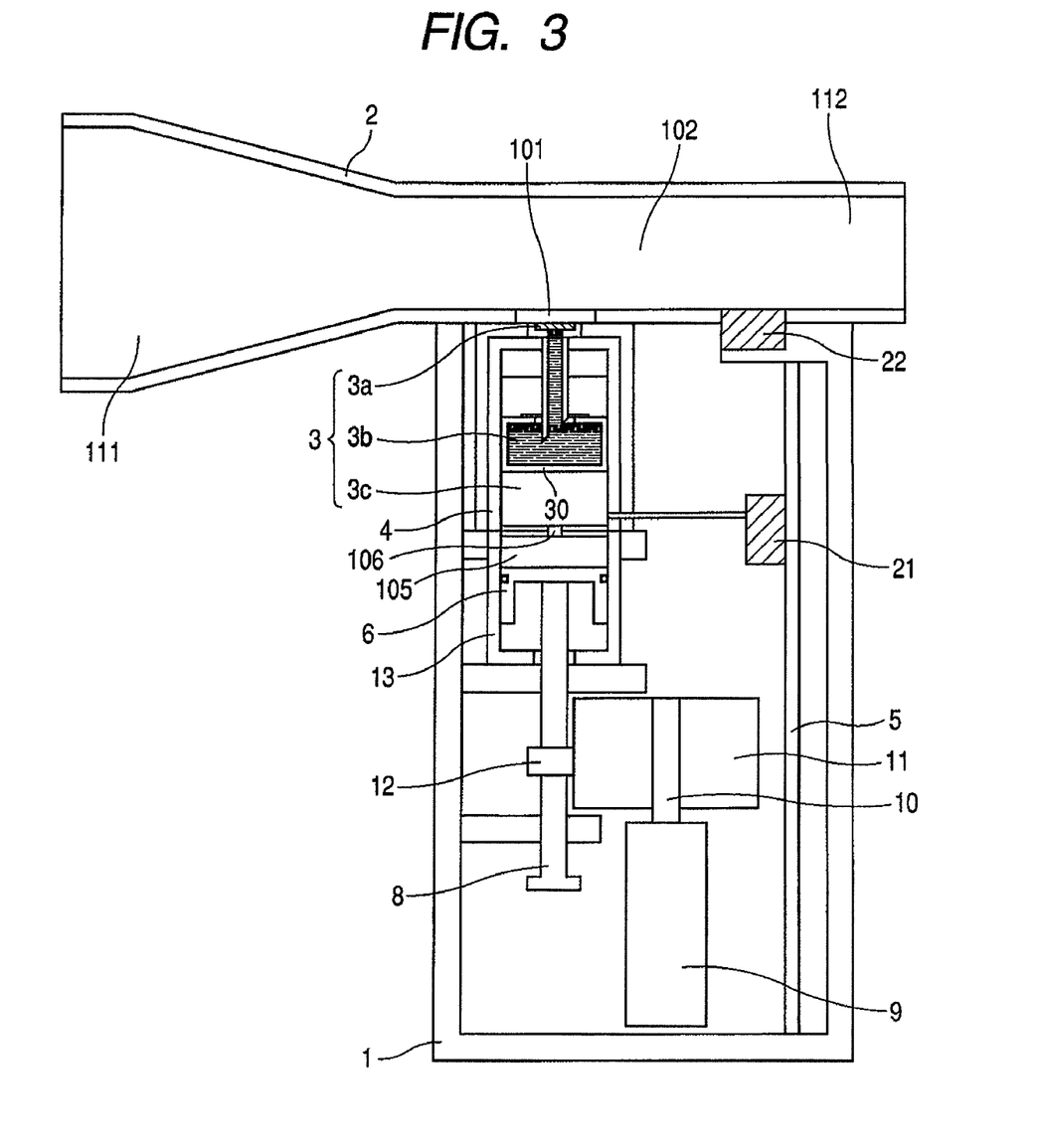
FIG. 3 is a sectional view showing an ejection device according to a third embodiment of the present invention.
Figure 4:
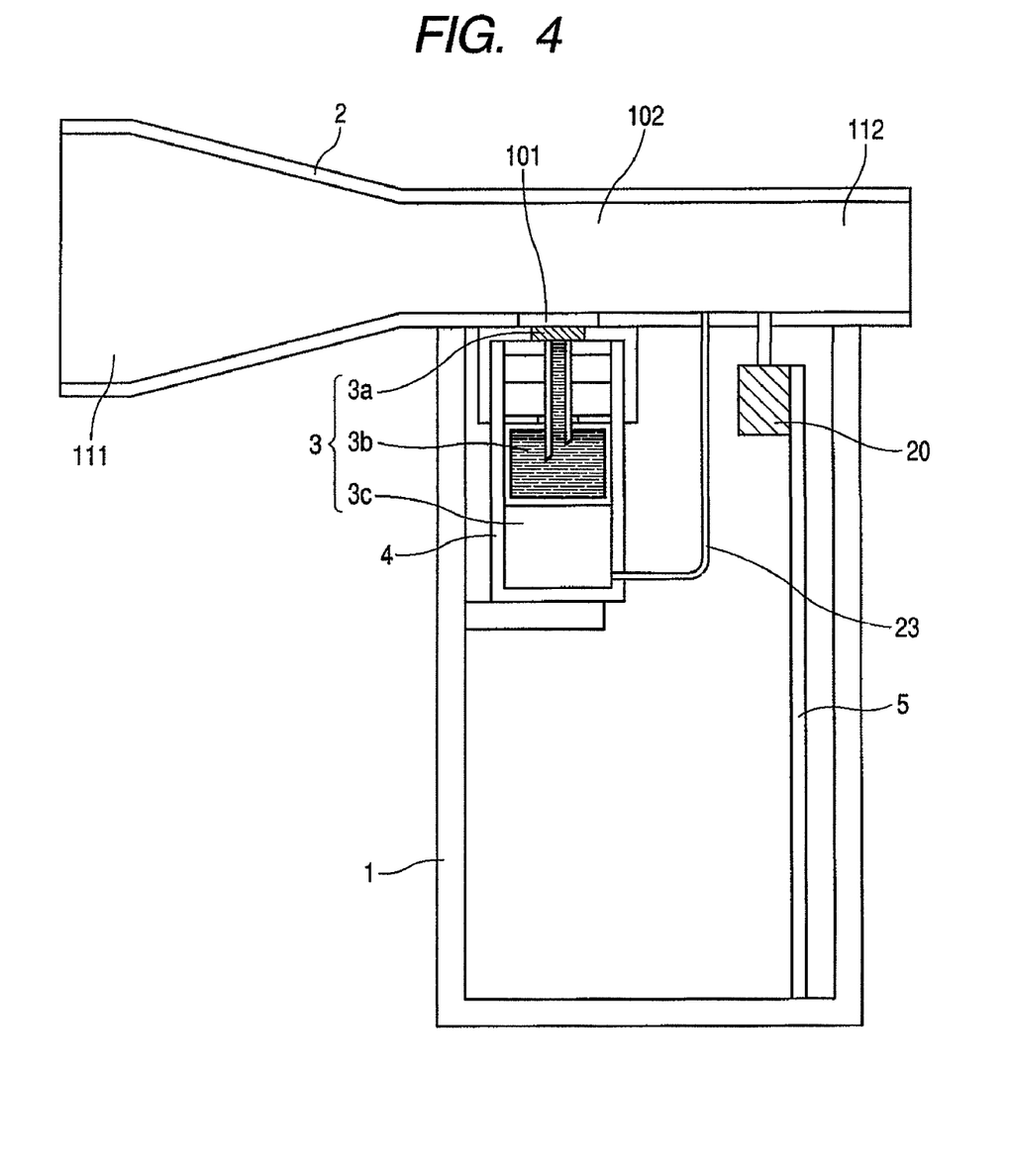
FIG. 4 is a sectional view showing an ejection device according to a fourth embodiment of the present invention.
Figure 5:
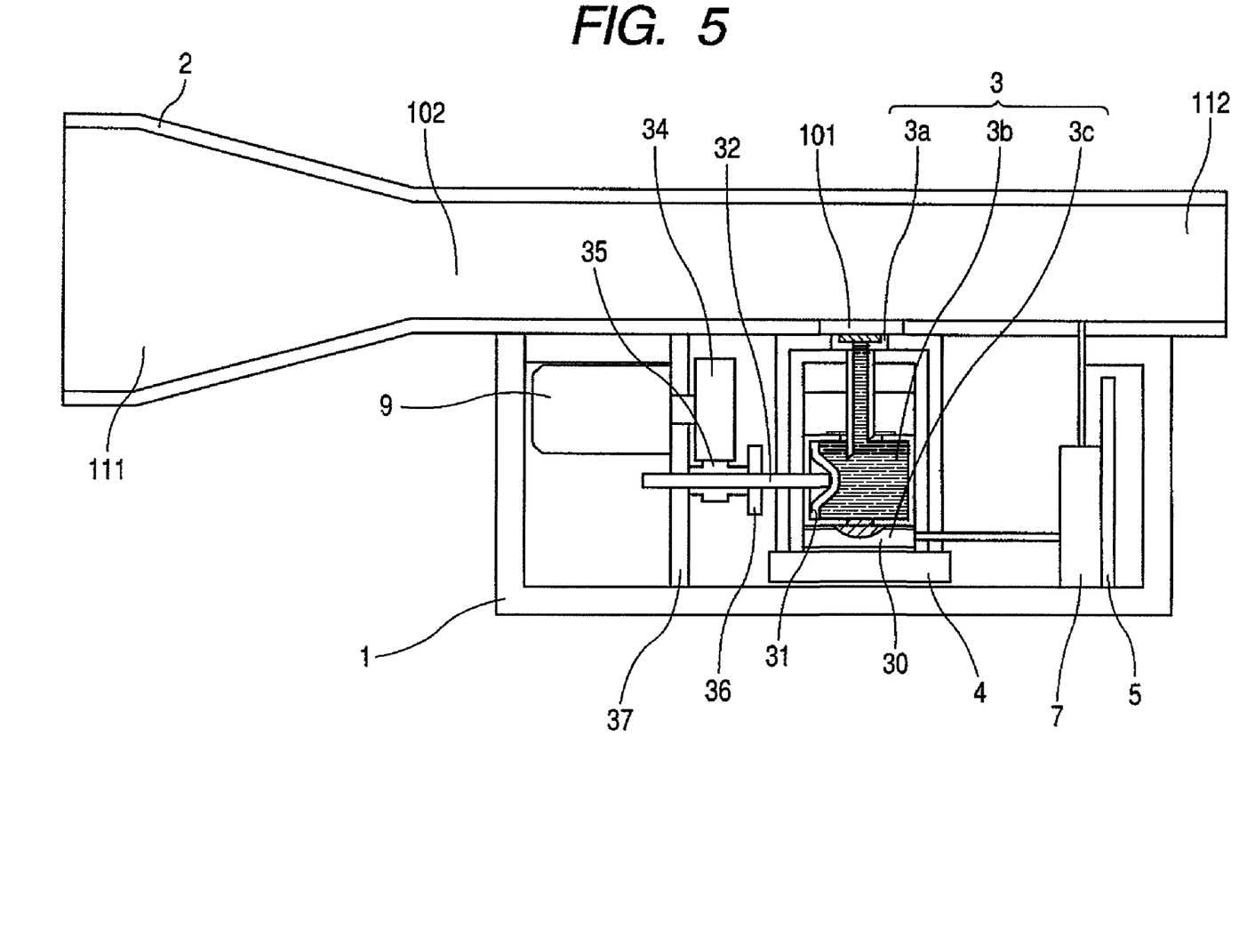
FIG. 5 is a sectional view showing an ejection device according to a fifth embodiment of the present invention.

FIG. 2 is a sectional view showing a second embodiment of the present invention. Like reference characters designate the same components as those of FIG. 1 and the description thereof will be omitted. While in the first embodiment shown in FIG. 1 the differential-pressure sensor 7 is used, in this embodiment, a negative pressure sensor 20 for measuring the pressure in the inhalation flow path 102 and a negative pressure sensor 21 for measuring the pressure in the air chamber 3c are used as individual negative pressure sensors. That is, while in the first embodiment a pressure difference between the pressure in the inhalation flow path 102 and the pressure in the air chamber 3c are directly measured by the differential-pressure sensor 7, in this embodiment, the pressures of those are respectively measured by the negative pressure sensors 20 and 21, and the pressure difference is calculated from the obtained pressures.

Operations and actions in this embodiment are substantially the same as those of the first embodiment. In the second embodiment, the pressure generated in the inhalation flow path 102 can be measured individually. Accordingly, it is possible to calculate an inhalation flow rate from the generated pressure because the sectional area of the inhalation flow path 102 of the mouthpiece 2 is fixed. In this manner, according to the change in inhalation flow rate, the ejection control can be performed for keeping the density of an inhalation mist including the liquid droplets to be ejected substantially constant. The density of the inhalation mist including the liquid droplets to be ejected is kept substantially constant, thereby making it possible to increase a liquid-droplet fixation rate with respect to the user's lungs.

FIG. 3 is a sectional view showing a third embodiment of the present invention. Like reference characters designate the same components as those of FIGS. 1 and 2 and the description thereof will be omitted. In this embodiment, the negative pressure sensor 20 for measuring the pressure in the inhalation flow path 102 according to the second embodiment is replaced with a flowmeter 22. While in the second embodiment the pressure in the inhalation flow path is directly measured by the negative pressure sensor 20, in the third embodiment, the pressure in the inhalation flow path is estimated based on the inhalation flow rate measured by the flowmeter 22. Further, while in the second embodiment the inhalation flow rate is calculated from the detected value of the negative pressure sensor 20, the third embodiment enables the inhalation flow rate to be directly read by the flowmeter 22. Operations and actions of this embodiment are substantially the same as those of the first embodiment.

FIG. 4 is a sectional view showing a fourth embodiment. Like reference characters designate the same components as those of FIGS. 1 to 3 and the description thereof will be omitted. In this embodiment, an inner side of the inhalation flow path 102 of the mouthpiece 2 and the air chamber 3*c* contacting with the flexible film of the liquid medicine tank 3*b* are directly connected in communication to each other through a tube 23, thereby keeping the pressure in the vicinity of the ejection head 3*a* of the mouthpiece 2 and the pressure in the air chamber 3*c* substantially constant at all times. The actions related to the ejection are the same as those of the first embodiment. This embodiment can be achieved at remarkably low cost for preventing the leakage of the liquid medicine from the ejection unit 3. This embodiment suits for the ejection requiring few quick refilling actions, and is therefore effective for the medicine which is sufficient when ejected in small amount.

FIG. 5 is a sectional view showing a fifth embodiment. Like reference characters designate the same components as those of FIGS. 1 to 4 and the description thereof will be omitted. Also in this embodiment, the mouthpiece 2 can be fixed to the main body case 1 so as to be detachable therefrom, and the mouthpiece 2 is provided with the hole 101 connecting the inhalation flow path 102 to the medicine ejection unit 3 in order for the ejection liquid droplets to be ejected from the medicine ejection unit 3 into the inhalation flow path 102 inside the mouthpiece 2. Facing the hole 101 provided to the mouthpiece 2, the ejection head 3*a* of the medicine ejection unit 3 is arranged.

The medicine ejection unit 3 includes the ejection head 3*a*, the liquid medicine tank 3*b*, and the air chamber 3*c* integrated with each other. The liquid medicine tank 3*b* containing the liquid medicine has the flexible film 30 as a part thereof and an elastic film 31 on another surface thereof. The main body case 1 includes the medicine ejection unit attachment portion 4. On a lateral side of the attachment portion 4, there is provided a screw shaft 32 having a screw configuration on an outer periphery thereof for forcing in the elastic film 31 of the liquid medicine tank 3*b*. The screw shaft 32 is provided with a gear 35 having an inner periphery engaging with the screw shaft 32 and an outer periphery engaging with a pinion gear 34 integrated and attached to an output shaft end of the pressure adjusting motor 9. The gear 35 is held so as not to move in a thrust direction with respect to a screw shaft holding plate 36 and a pressure adjusting motor holding plate 37, and the gear 35 is rotatable at its position. Accordingly, due to the rotation of the pressure adjusting motor 9, the screw shaft 32 reciprocates horizontally.

The air chamber 3*c* is connected to the pressure measuring hole of the differential-pressure sensor 7 arranged on the control board 5, and the other pressure measuring hole of the differential-pressure sensor 7 is connected to the inhalation flow path 102 of the mouthpiece 2.

The ejection head 3*a* is electrically connected to the control board 5, thereby controlling ejection of the liquid droplets from the ejection head 3*a*. The ejection head 3*a*, the control board 5, the pressure adjusting motor 9, and other electrically driven portions are driven by a battery (not shown) provided in the main body case 1.

Operations and actions of this embodiment will be described.

First, the user attaches the medicine ejection unit 3 and the mouthpiece 2 to the main body 1 in the same manner as that of the first embodiment. At this time, owing to the attachment detection function of the main body 1, the power of the main body is turned on.

Next, the elastic film 31 provided to the liquid medicine tank 3*b* is pushed into the liquid medicine tank 3*b* by a movement of the screw shaft 32 owing to the rotation of the pressure adjusting motor 9, thereby increasing the pressure inside the liquid medicine tank 3*b*. Owing to the increase in pressure, the flexible film 30 bulges toward the air chamber 3*c* side. At the same time, at the orifice (ejection opening) surface of the ejection head 3*a*, the medicine is pushed out (restoring action). As a result, a layer of the medicine is evenly generated on the orifice surface to be ready for ejection.

Next, when the user starts the inhalation, the pressure in the inhalation flow path 102 becomes negative. In this embodiment as well, when the pressure exceeds a certain threshold value, it is judged that the inhalation is started, and then the ejection from the ejection unit 3 is started. At this time, as a matter of course, the orifice surface on the surface of the ejection head 3*a* is subjected to the negative pressure, thereby generating a force in a direction in which the leakage occurs. In order to cancel this force, based on the detected value of the differential-pressure sensor 7, the pressure adjusting motor 9 arranged on a lateral side of the liquid medicine tank 3*b* is driven so that the screw shaft 32 is moved in such a direction that the elastic film 31 is returned to an initial position, which is the position before the restoring action (before pushing in). Then, according to the negative pressure generated in the inhalation flow path 102, the pressure in the liquid medicine tank 3*b* becomes negative so as to reduce the negative pressure applied to the liquid medicine on the nozzle surface. This also affects the air chamber 3*c* which is isolated from the liquid medicine tank 3*b* by the flexible film 30. Therefore, the pressure in the air chamber 3*c* becomes negative. The pressure balance is set such that the pressure in the air chamber 3*c* is higher than the pressure in the inhalation flow path 102 by about 0.1 kPa.

On the other hand, when the flow rate in the inhalation flow path 102 decreases and the pressure therein approaches the atmospheric pressure, the pressure adjusting motor 9 is rotated backward to perform control so as to increase the pressure in the liquid medicine tank 3*b*. That is, the pressure adjusting motor 9 is rotated in such a direction that reduces the volume of the air chamber 3c, and again, the screw shaft is adjusted to a position where the pressure in the air chamber 3c is higher than the pressure in the inhalation flow path 102 by about 0.1 kPa. In a case where the pressure difference therebetween deviates from the desired pressure difference by about 0.03 kPa or more, the adjustment is performed such that the pressure difference is within a range of 0.1 kPa±0.02 kPa. During the inhalation by the user, the above-mentioned actions are repeated.

In the same manner as that of the first embodiment, based on the data on the prescription, the ejection device main body judges that the predetermined amount has been ejected and notifies the user of the completion of the inhalation by emitting a completion signal such as light, sound, or vibration.

The present invention is not limited to the above embodiments, and various changes and modifications can be made within the spirit and scope of the present invention. Therefore to apprise the public of the scope of the present invention, the following claims are made.

This application claims the benefit of Japanese Patent Application No. 2005-265129, filed Sep. 13, 2005 which is hereby incorporated by reference herein in its entirety.

What is claimed is:

1. An inhaler, comprising:
   an inhalation flow path having a suction port and an air intake opening, said inhalation flow path being constructed such that air is introduced from the air intake opening when a user starts inhalation via the suction port;
   a liquid medicine storage section for storing the liquid medicine;
   an ejection head, which communicates with the liquid medicine storage section, for ejecting the liquid medicine from an ejection opening into the inhalation flow path in a form of liquid droplets, the ejection head ejecting the liquid medicine by using at least one of heat energy and piezoelectric energy;
   a sensor capable of measuring a pressure difference between the inhalation flow path and the liquid storage section;
   a pressure changer for increasing and decreasing pressure in the liquid medicine storage section; and
   a controller for controlling the pressure changer so as to maintain the pressure difference measured by the sensor within a predetermined range before, during and after the inhalation.

2. The inhaler according to claim 1, wherein a pressure value in the liquid medicine storage section is higher than a pressure value in the inhalation flow path by 0 to 0.5 kPa.

3. The inhaler according to claim 1, wherein the sensor comprises a differential-pressure sensor for measuring the pressure difference between the pressure in the inhalation flow path and the pressure in the liquid medicine storage section.

4. The inhaler according to claim 1, wherein the sensor comprises negative pressure sensors for measuring the pressure in the inhalation flow path and the pressure in the liquid medicine storage section, respectively.

5. The inhaler according to claim 1, wherein the sensor comprises a flow rate sensor for measuring a flow rate in the inhalation flow path; and a negative pressure sensor for measuring the pressure in the liquid medicine storage section.

6. The inhaler according to claim 1, wherein at least a part of the liquid medicine storage section comprises a deformable member and the pressure changer increases and decreases volume of the liquid medicine storage section.

7. The inhaler according to claim 1, wherein the controller controls the pressure changer to decrease the pressure in the liquid medicine storage section during the inhalation and to increase the pressure in the liquid storage section after the inhalation.

8. An inhaler, comprising:
   an inhalation flow path having a suction port and an air intake opening, said inhalation flow path being constructed such that air is introduced from the air intake opening when a user starts inhalation via the suction port;
   a liquid medicine storage section for storing the liquid medicine;
   an ejection head, which communicates with the liquid medicine storage section, for ejecting the liquid medicine from an ejection opening into the inhalation flow path, the ejection head ejecting the liquid medicine by using at least one of heat energy and piezoelectric energy;
   an air chamber partitioned from the liquid medicine storage section by a flexible film;
   a sensor capable of measuring a pressure difference between the inhalation flow path and the air chamber;
   a member capable of increasing and decreasing a pressure in the air chamber; and
   a controller for controlling the member so as to maintain the pressure difference measured by the sensor within a predetermined range before, during and after the inhalation.

9. The inhaler according to claim 8, wherein the sensor comprises a differential pressure sensor having pressure measuring holes provided in the inhalation flow path and the air chamber, respectively.

10. The inhaler according to claim 8, wherein the sensor comprises a negative pressure sensor having a pressure measuring hole provided in the inhalation flow path, and a negative pressure sensor having a pressure measuring hole provided in the air chamber.

11. The inhaler according to claim 8, wherein the sensor comprises a flow rate sensor for measuring a flow rate in the inhalation flow path, and a negative pressure sensor having a pressure measuring hole provided in the air chamber.

12. The inhaler according to claim 8, wherein the controller controls the member to decrease the pressure in the air chamber during the inhalation and to increase the pressure in the air chamber after the inhalation.

* * * * *